United States Patent [19]

Stiller et al.

[11] 4,052,436

[45] Oct. 4, 1977

[54] FLUORENE-2-ACETIC ACIDS AND DERIVATIVES, PROCESS AND METHOD OF USING

[75] Inventors: Eric T. Stiller, Sarasota, Fla.; Seymour D. Levine, North Brunswick, N.J.; Pacifico A. Principe, South River, N.J.; Patrick A. Diassi, Westfield, N.J.

[73] Assignee: E. R. Squibb & Sons, Inc., Princeton, N.J.

[21] Appl. No.: 715,033

[22] Filed: Aug. 17, 1976

Related U.S. Application Data

[60] Division of Ser. No. 510,850, Sept. 30, 1974, Pat. No. 3,989,841, which is a continuation of Ser. No. 298,102, Oct. 16, 1972, Pat. No. 3,856,977, which is a continuation-in-part of Ser. No. 70,913, Sept. 9, 1970, Pat. No. 3,859,340.

[51] Int. Cl.$^2$ .............. C07C 69/76; A61K 31/235

[52] U.S. Cl. .............. 560/52; 260/465 R; 260/465 F; 260/465 G; 260/515 R; 260/515 A; 260/518 R; 260/518 A; 260/520 D; 560/21; 560/43; 560/102; 424/308; 424/309; 424/317; 424/319

[58] Field of Search .............. 260/515 R, 515 A, 469, 260/471 R, 473 F, 518 R, 518 A, 520 D

[56] References Cited

U.S. PATENT DOCUMENTS

| | | | |
|---|---|---|---|
| 3,903,145 | 9/1975 | Levine et al. | 260/518 A |
| 3,987,088 | 10/1976 | Hodson et al. | 260/520 D |

OTHER PUBLICATIONS

Dahm et al., Chemical Abstracts, 105004 (p), vol. 79, (1973).

*Primary Examiner*—James O. Thomas, Jr.
*Assistant Examiner*—G. T. Breitenstein
*Attorney, Agent, or Firm*—Lawrence S. Levinson; Merle J. Smith; Donald J. Barrack

[57] ABSTRACT

Fluorene-2-glyoxylic acid, 7-substituted derivatives thereof, and ester derivatives thereof are disclosed as useful for the treatment of inflammatory conditions.

5 Claims, No Drawings

FLUORENE-2-ACETIC ACIDS AND DERIVATIVES, PROCESS AND METHOD OF USING

This is a division of application Ser. No. 510,850, filed Sept. 30, 1974, now U.S. Pat. No. 3,989,841, issued Nov. 2, 1976; which is a continuation of application Ser. No. 298,102, filed Oct. 16, 1972, now U.S. Pat. No. 3,856,977, issued Dec. 24, 1974; which is a continuation-in-part of application Ser. No. 70,913, filed Sept. 9, 1970, now U.S. Pat. No. 3,859,340, issued Jan. 7, 1975.

This invention relates to new fluorene-2-acetic acid derivatives having the structure

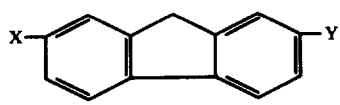

wherein X is hydrogen, lower alkyl, hydroxyl, lower alkoxy, halogen, amino, trifluoromethyl or nitro and Y is

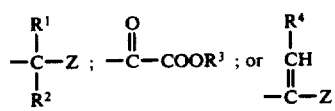

wherein Z is —COOH, —COOR$^5$ or —CN; R$^1$ is hydrogen, hydroxy, lower alkyl or monocyclic cycloalkyl; R$^2$ is hydrogen or alkyl containing from one to about twelve carbon atoms or monocyclic cycloalkyl; R$^3$ is hydrogen or lower alkyl; R$^4$ is hydrogen, lower alkyl or monocyclic cycloalkyl; and R$^5$ is lower alkyl, aryl, aralkyl, or a metallic ion. Where X is hydrogen, halogen, nitro, or amino, Y is other than CH$_2$COOH.

Further in accordance with the present invention, a method is provided for treating inflammatory conditions and conditions responsive to treatment with anti-inflammatory agents, which comprises administering an anti-inflammatory amount of the novel compounds above described; of fluorene-2-acetic acid; or of the 7-halo, 7-nitro, or 7-amino substituted fluorene-2-acetic acid.

Fluorene-2-acetic acid and its 7-halo, 7-nitro and 7-amino derivatives are known. The preparation of these compounds is taught, for example, by Ogato et al in *J. Org. Chem.*, 18, 1329 (1953).

The term "lower alkyl" as employed herein includes both straight and branched chain radicals of up to and including eight carbon atoms, for instance, methyl, ethyl, propyl, isopropyl, butyl, s-butyl, t-butyl, isobutyl, pentyl, hexyl, isohexyl, heptyl, 4,4-dimethylpentyl, octyl, 2,2,4-trimethylpentyl and the like. The lower alkyl group can include substituents such as aryl.

The halogen can be F, Br, Cl or I.

The term "lower alkoxy" includes straight and branched chain radicals of the structure RO— wherein R includes any of the above lower alkyl groups.

The "amino" groups may include unsubstituted amino or mono- or di-lower alkyl amino groups, wherein lower alkyl is as defined above, such as amino, methylamino, ethylamino, isopropylamino, heptylamino, dimethylamino, diethylamino, methylethylamino, methylbutylamino, ethyl-i-propylamino, acylamino, wherein the acyl group is derived from hydrocarbon carboxylic acids containing less then 12 carbon atoms, and may be exemplified by the lower alkanoic acids (e.g., formic, acetic, propionic, butyric, valeric, trimethyl acetic and caproic acids), the lower alkenoic acids (e.g., acrylic, methacrylic, crotonic, 3-alkenoic and senecioic acids), the monocyclic aryl-carboxylic acids (e.g., benzoic and toluic acids), the monocyclic aryl-lower alkanoic acids [e.g., phenacetic, β-phenylpropionic, α-phenylbutyric, and 5-(p-methylphenyl) pentanoic acids], the cycloalkyl carboxylic acids (e.g., cyclobutane carboxylic acid, cyclopentane carboxylic acid and cyclohexane carboxylic acid), the cycloalkenyl carboxylic acids (e.g., 2-cyclobutene carboxylic acid and 3-cyclopentene carboxylic acid), the cycloalkyl and cycloalkenyl-lower alkanoic acid [e.g., cyclohexaneacetic, α-cyclopentanebutyric, 2-cyclopenteneacetic and 3-(3-cyclohexene) pentenoic acid], and the like.

The term "monocyclic aryl" as employed herein includes monocyclic carbocyclic aryl radicals, for instance, phenyl and substituted phenyl radicals, including lower alklyphenyl, such as tolyl, ethylphenyl, butylphenyl and the like, di(lowr alkyl)phenyl (e.g., dimethylphenyl, 3,5-diethylphenyl, and the like), halophenyl (e.g., chlorophenyl, bromophenyl, and 2,4,5-trichlorophenyl) and nitrophenyl.

The term "monocyclic cycloalkyl" includes cyclic radicals containing from 3 to 6 ring members (e.g., cyclopropyl, cyclobutyl, cyclopentyl and cyclohexyl).

Examples of compounds falling within the present invention include, but are not limited to, the following:

1.

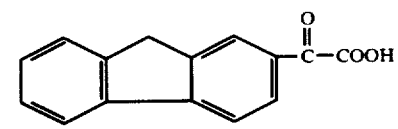

2.

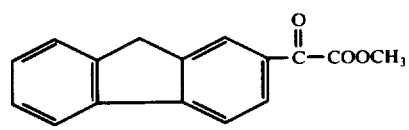

3.

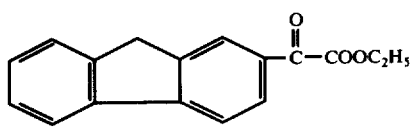

4.

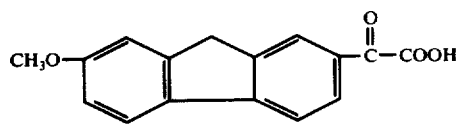

5.

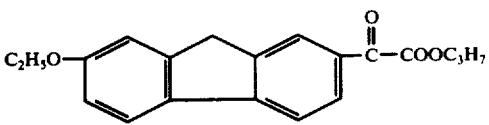

6.

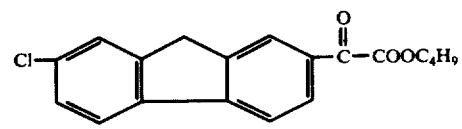

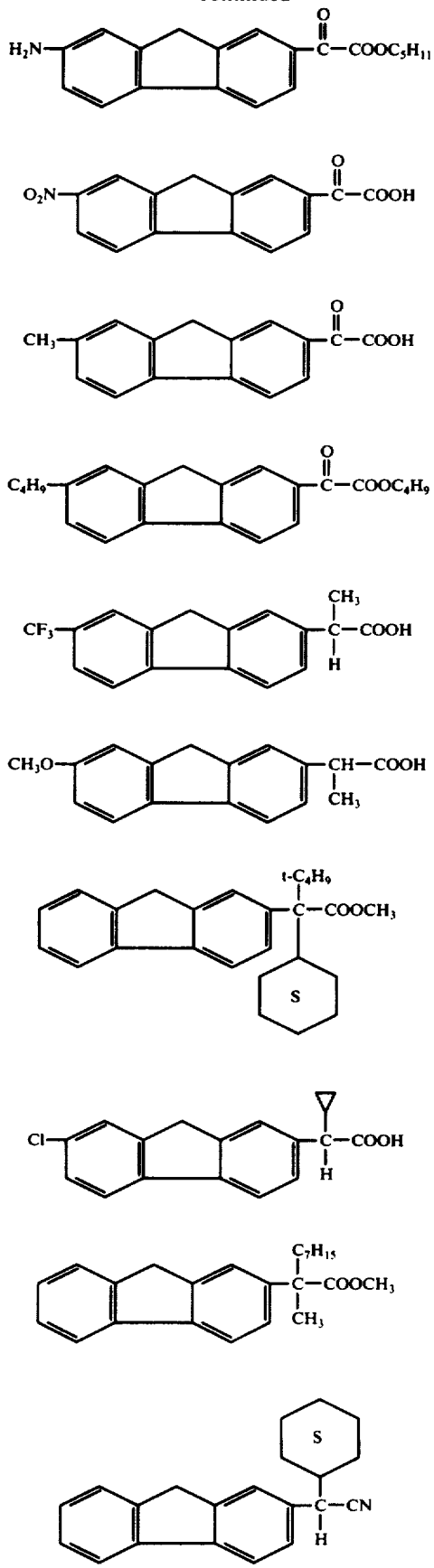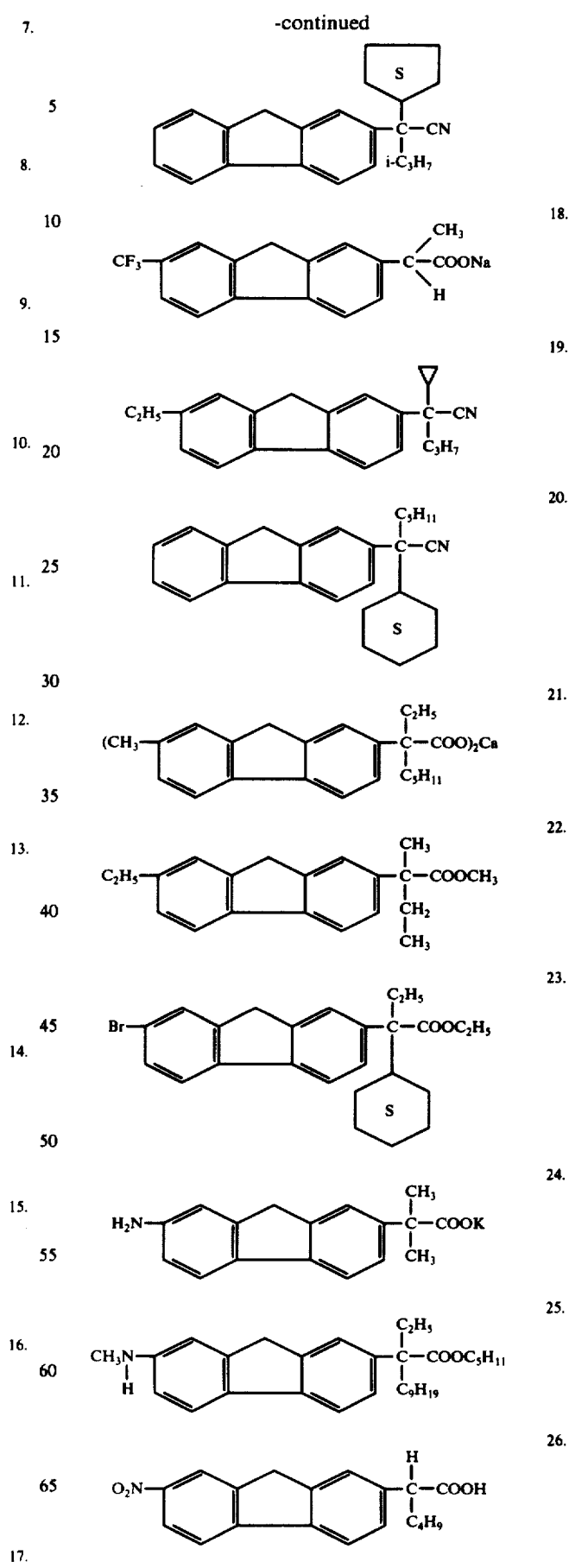

27. 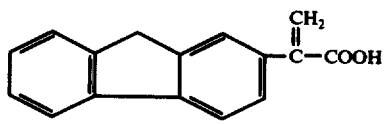

28. 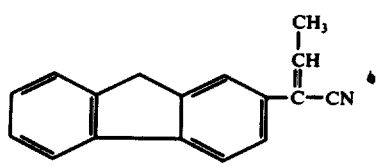

29. 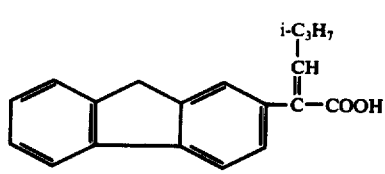

30. 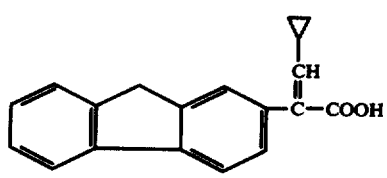

31. 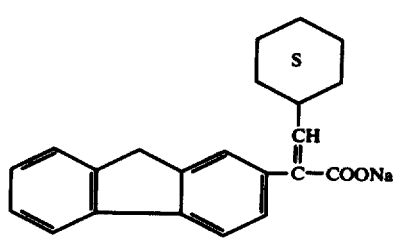

32. 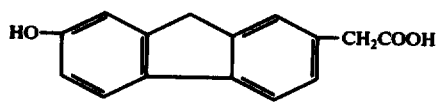

33. 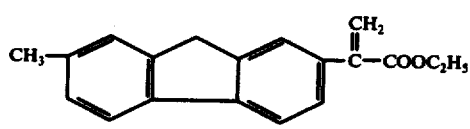

34. 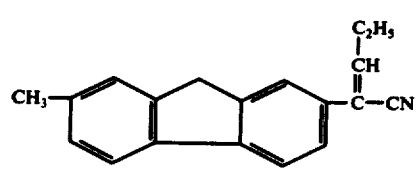

35. 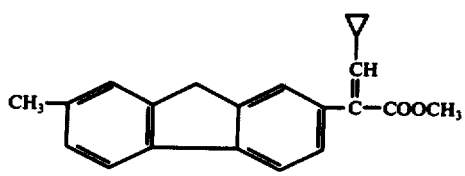

36. 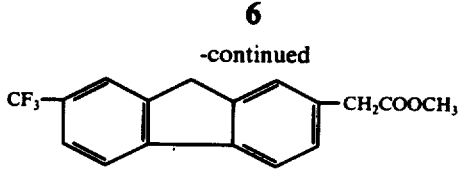

37. 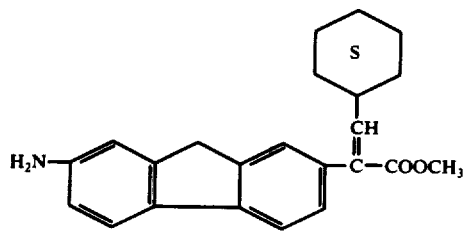

38. 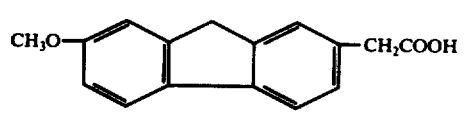

39. 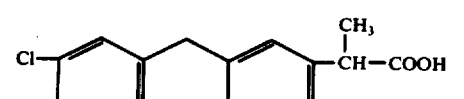

40. 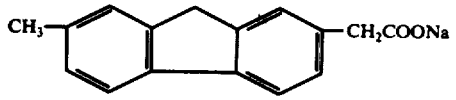

The compounds of formula I wherein Y is

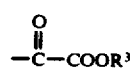

can be prepared by reacting fluorene or a 7-substituted fluorene with a lower alkyl oxalyl halide having the structure

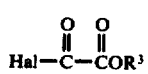

in the presence of a catalyst such as aluminum chloride or other Friedel-Crafts catalyst to form a compound of the structure

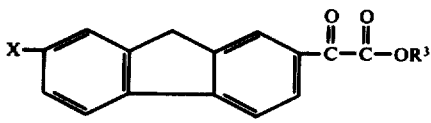 III wherein R³ is lower alkyl, such as ethyl.

The above reaction is carried out in the presence of an inert solvent such as ethylene dichloride, carbon disulfide, carbon tetrachloride, or petroleum ether, at a temperature within the range of from about −5° to about +15° and preferably from about 5° to about 10°. The fluorene compound is employed in a molar ratio to the oxalyl compound of within the range of from about 0.9:1 to about 0.75:1 and preferably from about 0.9:1 to about 0.85:1.

The COOR³ in Compound III wherein R³ is alkyl can be converted to the corresponding carboxyl group to form a fluorene-2-glyoxylic acid by basic hydrolysis, that is by reacting a fluorene derivative of structure III with a base such as an alkali metal or alkaline earth metal hydroxide or alkoxide, such as sodium hydroxide or sodium methoxide, in the presence of an aqueous alcohol containing up to about five carbon atoms, such as methanol or ethanol. These carboxylic acids can be esterified to form the corresponding esters by conventional methods known in the art.

Compounds of the structure I wherein Y is

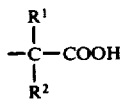

can be prepared by reacting a fluorene derivative of structure III wherein R³=H in solution in ethyl ether or other solvents such as tetrahydrofuran, isopropyl ether, or methylal, with a Grignard reagent (R²MgHal) such as CH₃MgI, in ethyl ether to form a compound of the structure

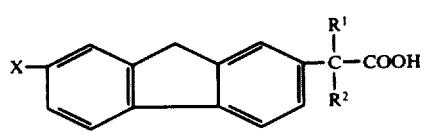

IV wherein R¹ is hydroxyl.

Compounds corresponding to compound IV wherein R¹ is lower alkyl or cycloalkyl can be prepared as follows: esters of compounds of the type IV where R₁ is hydrogen are alkylated wih an alkyl halide or cycloalkyl halide in dimethylformamide or diglyme in the presence of a base such as sodium hydride.

Compounds of the structure I wherein Y is

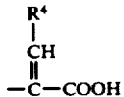

i.e., α-methylene fluorene-2-acetic acid, can be prepared by reacting an α-substituted-α-hydroxyfluorene-2-acetic acid of structure IV containing a hydrogen on the carbon vicinal to the hydroxyl group with a mineral acid such as hydrochloric acid or sulfuric acid in dioxane or other solvent such as tetrahydrofuran.

Compounds of structure I wherein Y is

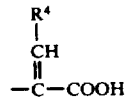

can also be prepared by reacting compounds of structure III in a Wittig reaction with a substituted triphenylphosphonium halide such as methyltriphenylphosphonium bromide.

Compounds of formula I wherein Y is

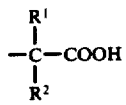

wherein R¹ is hydrogen can be prepared by catalytic hydrogenation of the above compounds.

In addition, in accordance with the present invention, compounds of the structure

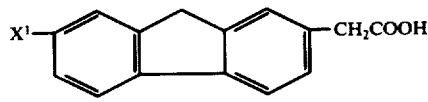

V are provided wherein X¹ is hydroxyl, lower alkyl, lower alkoxy, and trifluoromethyl.

Compounds of structure V can be prepared by reacting a 7-substituted fluorene-2-glyoxylic acid or ester of structure III and fluorene-2-glyoxylic acid with hydrazine or hydrazine hydrate in a modified Wolf-Kishner reaction at a temperature within the range of from about 130° to about 180° C until solution is achieved, cooling the solution to a temperature within the range of from abut 50° to about 60° C and treating the cooled solution with a base such as an alkali metal hydroxide or alkoxide such as potassium hydroxide or sodium ethoxide.

In preparing compounds of structure V, the fluorene compound is employed in a molar ratio to the hydrazine compound of within the range of from about 0.01:1 to about 0.2:1 and preferably from about 0.01:1 to about 0.05:1. The base is employed in a molar ratio to the fluorene compound of within the range of from about 0.15:1 to about 0.3:1 and preferably from about 0.2:1 to about 0.25:1.

Compounds of the structure V and compounds of formula I wherein Y is

may be prepared by reacting the appropriately substituted fluorene-2-carboxylic acid halide with a diazoalkane to form the corresponding diazoketone followed by a Wolff rearrangement to an ester and hydrolysis.

Compounds of the structure VI

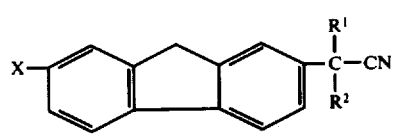

VI wherein R¹ is other than hydroxyl can be prepared by alkylating a 2-fluoreneacetonitrile of the structure

VII

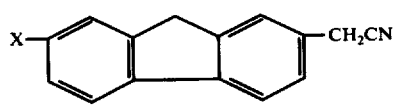

with an alkyl or cycloalkyl halide in the presence of a base such as sodium hydride in an inert solvent such as dimethylformamide or diglyme.

The cyano group of compound VI can be hydrolyzed to a carboxyl group.

Compounds of the structure I wherein Y is

wherein R² is other than hydrogen can be prepared by reacting a 2-acyl fluorene of the structure

VIII

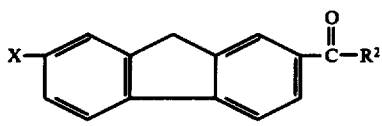

with an alkali metal cyanide such as sodium cyanide or hydrogen cyanide in an acidic medium.

Compounds of the structure I wherein Y is

can be prepared by dehydrating an α-hydroxy fluorene-2-acetonitrile of the structure

IX

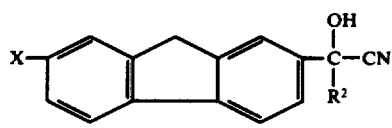

which contains hydrogen on the carbon vicinal to the hydroxyl group with a mineral acid or with phosphorous oxychloride in a suitable olvent. The resulting compounds of the structure

X

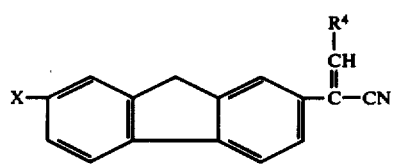

can be converted to the corresponding carboxylic acids XI by catalytic hydrogenation followed by basic hydrolysis.

XI

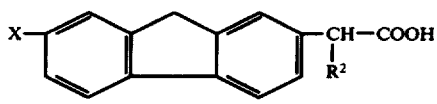

Compounds of formula I wherein Y is

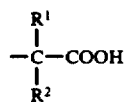

or —CH₂COOH can be converted to the corresponding 7-hydroxylated compounds by fermentation in the presence of an appropriate organism.

The enzymatic 7-hydroxylation can be accomplished either by including the fluorene substrate in a growing or mature culture of an appropriate microorganism, or by treating the substrate with the cells, spores or mycelium of such a culture separated from the growth medium or hydroxylating enzymes separated from cells of such microorganisms.

Suitable microorganisms for hydroxylation include members of the genera: Aspergillus (e.g., *A. ochraceus, A. nidulans, A. niger*), Rhizopus (e.g., *R. arrhizus*), Syncephalstrum (e.g., *S. racemosumt. Thamnidium (e.g., I. elegans*) Mucor (e.g., *M. adriaticus*), Trichothecium (e.g., *T. roseum*), Phycomyces (e.g., *P. nitens*), Penicillium (e.g., *P. expansum*), Blakeslea (e.g., *B. trispora*), Cercospora (e.g., *C. melonis*), Cunninghamella (e.g., *C. blakesleeana*), Botrytis (e.g., *B. cinerea*), or Corticium (e.g., *C. sasaki*).

If the microorganism is used per se, it is grown aerobically in a suitable nutrient medium, as known in the art; the substrate being added either at the beginning or sometime during the culturing process.

In general, the conditions of culturing the microorganisms for the purpose of this invention are the same as those of culturing microorganisms for the production of antibiotics or vitamins. Thus, the microorganism is grown in contact with (in or on) a suitable nutrient medium in the presence of an adequate supply of oxygen (air). A suitable nutrient medium essentially comprises a source of nitrogenous factors and an assimilable source of carbon and energy. The latter may be a carbohydrate, such as sucrose, molasses, glucose, maltose, starch or dextrin. The source of nitrogenous factors may be organic (e.g., soybean meal, corn steep liquor, meat extract, distillers solubles, peptones and/or yeast extract) or synthetic (i.e., composed of simple, synthesizable organic and inorganic compounds such as ammonium salts, alkali nitrates, amino acids or urea).

The acid substrate, in aqueous, aqueous alcoholic solution or dimethylformamide solution, is added either prior to or during the culturing of the microorganism, if the microorganism is used per se, or to an aqueous medium containing the separated cells, spores or cell-free hydroxylating enzyme, if this procedure is employed. After about 1 to about 200 hours, depending on the concentration of this acid and enzyme, the reaction is substantially complete. The resulting 7-hydroxylated derivative can then be recovered by filtration or centrifugation (if solid) or by counter-current extraction.

These 7-hydroxylated compounds can also be prepared from the corresponding 7-amino compounds by diazotization as described hereinbefore.

Of the fluorene-2-acetic acid derivatives, α-methylfluorene-2-acetic acid is of particular interest. It has been found that each of the *d* and the *l* optical isomers, as well as the *dl* mixture, possesses anti-inflammatory activity.

The optical isomers of α-methylfluorene-2-acetic acid may be obtained in the normal way by resolution of the racemic mixture. This is done by reacting the mixture with an optically active base (the resolving agent) to yield diastereo-isomers — two salts with different rotatory values, solubilities, and melting points. Separation of the salts may be done by fractional crystallization. The salts may then be converted to the free acid by treatment with a mineral acid. Examples of optically active compounds that are useful as resolving agents are α-methylbenzylamine, cinchonidine, cinchonine, α-methylnaphthylamine, dehydroabietylamine, amphetamine, adn strychnine.

The fluorene-2-acetic acid derivatives of the invention form salts with organic bases, e.g. alkylamines such as methylamine, ethylamine, isopropylamine, glucamine, aniline, dimethylamine, etc., heterocyclic amines such as piperidine, morpholine, and the like, and with inorganic bases, e.g., ammonium hydroxide, alkali metal hydroxides such as sodium hydroxide, potassium hydroxide, etc., alkaline earth metal hydroxides such as calcium hydroxide, magnesium hydroxide, etc., alkali metal carbonates and bicarbonates such as sodium carbonate, potassium bicarbonate, etc. These basic salts may be used in the preparation and/or isolation of the products of this invention. When the product is produced in the form of a basic salt, neutralization with an acid, e.g., a mineral acid such as hydrochloric acid, or organic acid such as citric acid, will yield the compound in the acid form. Other basic salts may then be formed by reaction with the appropriate organic or inorganic base.

The compounds of this invention are useful as anti-inflammatory agents and are effective in the prevention and inhibition of granuloma tissue formation in warm blooded animals, for example, in a manner similar to indomethacin. They may be used to decrease joint swelling tenderness, pain and stiffness, in mammalian species, e.g., in conditions such as rheumatoid arthritis. A compound of this invention or a physiologically acceptable salt of the character described above may be compounded according to accepted pharmaceutical practice in oral dosage forms such as tablets, capsules, elixirs or powders for administration of about 100 mg to 2 gm per day, preferably 100 mg to 1 gm per day, in two to four divided doses. For example, about 150 mg/kg/day is effective in reducing paw swelling in rats.

For the purpose of illustrating how the compounds of this invention may be formulated for oral dosage, typical capsule and tablet formulations are described below, along with the procedure for their production.

| α-Methylfluorene-2-acetic acid; capsules | | |
|---|---|---|
| | | mg/capsule |
| α-methylfluorene-2-acetic acid | | 250.00 |
| lactose, U.S.P. | about | 47.60 |
| talc, U.S.P. | | 9.30 |
| magnesium stearate, U.S.P. | | 3.10 |
| | about | 310.00 |

Formulation of the capsules is accomplished by first mixing the active ingredient with a portion of the magnesium stearate. If it is necessary, the blend may be densified by slugging or other suitable means. The densified material is screened so that a uniform powder results. The remainder of the magnesium stearate, all of the talc, and all of the lactose are added and mixed. The formulation is added to No. 2 hard gelatin capsules (2 piece). The amount of lactose (and hence the capsule fill weight) may vary as the density of the α-methyl-fluorene-2-acetic acid varies.

| α-Methylfluorene-2-acetic acid; tablets | |
|---|---|
| | per tablet |
| Granulation No. 1 | |
| α-methylfluorene-2-acetic acid | 250 mg |
| starch, U.S.P. | 20 mg |
| povidone, N.F. | 20 mg |
| SD 3A alcohol | 0.1 ml* |
| lactose, U.S.P. | 185 mg |
| | 475 mg |

*does not appear in final product.

| | |
|---|---|
| Granulation No. 1 | 475 mg |
| starch, U.S.P. | 20 mg |
| magnesium stearate, U.S.P. | 2.5 mg |
| stearic acid, U.S.P. | 2.5 mg |
| | 500 mg |

Formulation of the tablets is accomplished by first mixing the active ingredient, the starch, and the lactose. The povidone is dissolved in the SD 3A alcohol. The mixed powder is granulated with the alcohol-povidone solution (additional alcohol is used as needed to obtain a uniformly wet mass). The wet mass is passed through a hammer mill at slow speed, with knives forward and with a ⅛ inch screen. After drying at 40° C the dry granulation is passed through a hammer mill at slow speed, with knives forward, and a 3/32 inch screen.

The granules obtained are mixed with the starch, magnesium stearate, and stearic acid to yield the final mix.

Tableting is accomplished using a 13/32 inch round standard concave punch and die.

The anti-inflammatory activities of fluorene-2-acetic acid and its derivatives may be tested by a carrageenin-induced edema assay. Carrageenin injected into the footpad of rats produces an edematous condition, due mainly to vaso-active mediators. The compound to be tested is administered orally and assessed for inhibition of the edema.

The compounds of the invention can also be employed as sun-screening agents and as intermediates for reaction with 6-aminopenicillanic acid and 7-aminocephalosporanic acid to produce new useful penicillins and cephalosporins.

The following examples represent specific embodiments of the present invention. All temperatures are given on the Centigrade scale.

EXAMPLE 1

Ethyl fluorene-2-glyoxylic acid

A suspension of aluminum chloride (75 g) in ethylene dichloride (200 ml) is cooled to 5° and treated dropwise over a 1 hour period with a solution of ethyl oxalyl chloride (50 g) and fluorene (53.6 g) in ethylene dichloride (200 ml); while maintaining the temperature below 10°. The reaction mixture is then stirred at room temperature (4 hours). The mixture is then poured into ice-water, acidified to pH 2.0 with 10% HCl and extracted with ether. The ether extracts are washed with water, dried (MgSO$_4$) and evaporated to give the title compound (86 g, mp 81–82°). The analytical sample is prepared by recrystallization from methanol: mp 81°–82°.

Anal. Calc'd. C, 76.67; H, 5.30; Found C, 76.56; H, 5.35.

EXAMPLES 2 to 7

By reacting ethyl oxalyl chloride with the 2-substituted fluorenes shown in the left hand column of Table I in accordance with the procedure of Example 1, the fluorene-2-glyoxylic acid esters shown in the right hand column of Table I are obtained.

Table I

| Example | X | X |
|---|---|---|
| 2 | $CH_3$ | $CH_3$ |
| 3 | (S) | (S) |
| 4 | $CH_3$ $\mid$ NH | $CH_3$ $\mid$ NH |
| 5 | $OC_2H_5$ | $OC_2H_5$ |
| 6 | Cl | Cl |
| 7 | $NH_2$ | $NH_2$ |

EXAMPLE 8

Fluorene-2-glyoxylic acid

A mixture of ethyl fluorene-2-glyoxylic acid (9.95 g) and sodium hydroxide (1.06g) in 50% aqueous ethanol (100 ml) is refluxed for 0.5 hour, cooled and acidified to pH 2.0 with 10% HCl. The reaction mixture is extracted with ether, and the ether extracts dried ($MgSO_4$) and evaporated. The residue is crystallized from benzenehexane (Darco) to give the title compound (7.1 g, mp 135°–137°). The analytical sample is prepared by recrystallization from benzenehexane: mp 139°–140°.

Anal. Calc'd. C, 75.62; H, 4.23; Found C, 75.76; H, 4.47.

EXAMPLES 9–14

Following the procedure of Example 2, but substituting the 7-substituted fluorene-2-glyoxylic acid esters of Examples 2 to 7 for the ethyl fluorene-2-glyoxylic acid, the corresponding 7-substituted fluorene-2-glyoxylic acids are produced, namely Table IA

| Example | X |
|---|---|
| 9 | $CH_3$ |
| 10 | (S) |
| 11 | $CH_3$ $\mid$ NH |
| 12 | $OC_2H_5$ |
| 13 | Cl |
| 14 | $NH_2$ |

EXAMPLE 15

Fluorene-2-acetic acid

A suspension of fluorene-2-glyoxylic acid (33.7 g) in hydrazine hydrate (50 ml) is refluxed until solution is achieved, cooled and treated with potassium hydroxide (33.7 g) in portions. The mixture is then refluxed for 1 hour, and the excess hydrazine removed by distillation. The residue is dissolved in water and extracted with chloroform. The aqueous layer is acidified to pH 2.0 with 10% HCl and extracted with ether. The ether extracts are washed, dried ($MgSO_4$) and evaporated to give the title compound (29.7 g, mp 184°–186°).

Anal. Calc'd. C, 80.33; H, 5.39; Found C, 80.67; H, 5.31.

EXAMPLES 16 to 18

Following the procedure of Example 15 and reacting the 7-substituted fluorene-2-glyoxylic acid shown in the left hand column of Table II (prepared as described in Examples 8 to 14) with hydrazine hydrate, the 7-substituted fluorene-2-acetic acid shown in the right hand column of Table II is obtained.

Table II

| Example | X' | X' |
|---|---|---|
| 16 | $C_5H_{11}$ | $C_5H_{11}$ |
| 17 | $C_2H_5$ | $C_2H_5$ |
| 18 | $OCH_3$ | $OCH_3$ |

EXLAMPLE 19

α-Methyl-α-hydroxyfluorene-2-acetic acid

A cooled solution of fluorene-2-glyoxylic acid (4.5 g) in ether (150 ml) is treated dropwise over a 45 minute period with Grignard reagent prepared from magnesium (2.1 g) and methyl iodide (6.5 ml) in ether (145 ml). The mixture is then stirred for 2 hours at room temperature and poured into ice water. The mixture is treated with 250 ml 50% acetic acid and finally acidified to pH 2.0 with 10% HCl. The ether layer is separated, and the aqueous extracted with additional ether. The combined ether extracts are washed with sodium chloride solution and water, dried (MgSO$_4$) and evaporated to give the title compound (3.7 g, mp 164°-168°). Recrystallization from ethyl acetate-hexane raises the mp to 170°-171°, λ$^{KBr}$ 3400 cm$^{-1}$.

Anal. Calc'd. C, 75.54; H, 5.55; Found C, 75.28; H, 5.44.

EXAMPLES 20 to 25

By reacting the 7-substituted fluorene-2-glyoxylic acid shown in the left hand column of Table III with the Grignard reagent shown in the middle column, employing the procedure described in Example 19 the α-alkyl-α-hydroxyfluorene-2-acetic acid shown in the right hand column of Table III is obtained.

Table IV

| Example | X | R$^4$ |
|---|---|---|
| 27 | Cl | H |
| 28 | NH$_2$ | CH$_3$ |
| 29 | NO$_2$ | C$_2$H$_5$ |

EXAMPLE 30

α-Methylene fluorene-2-acetic acid

A mixture of sodium hydride (0.48g.) and dimethylsulfoxide (5ml.) is stirred and heated at 70°-80° until the evolution of hydrogen ceases. The cooled solution is treated with methyltriphenylphosphonium bromide (7.14g) in dimethylsulfoxide (10ml.), stirred for 10 minutes and treated with ethyl fluorene-2-glyoxylic acid (5.32g.). The reaction mixture is stirred for 1 hr., the solvent evaporated and the residue extracted with ether after the addition of water. The ether extracts are washed with water, dried (MgSO$_4$) and evaporated. The residue is hydrolyzed by refluxing it in 50% methanol (50ml.) containing potassium hydroxide (5g.) for 3

Table III

| Example | X | R$^2$ | Hal | X | R$^2$ |
|---|---|---|---|---|---|
| 20 | N(CH$_3$)$_2$ | i-C$_3$H$_7$ | I | N(CH$_3$)$_2$ | i-C$_3$H$_7$ |
| 21 | CH$_3$ | (thienyl) | Br | CH$_3$ | (thienyl) |
| 22 | OC$_2$H$_5$ | (cyclopropyl) | Cl | OC$_2$H$_5$ | (cyclopropyl) |
| 23 | Cl | CH$_3$ | I | Cl | CH$_3$ |
| 24 | NH$_2$ | C$_2$H$_5$ | Cl | NH$_2$ | C$_2$H$_5$ |
| 25 | NO$_2$ | C$_3$H$_7$ | I | NO$_2$ | C$_3$H$_7$ |

EXAMPLE 26

α-Methylenefluorene-2-acetic acid

A solution of α-methyl-α-hydroxyfluorene-2-acetic acid (5.7 g) and sulfuric acid (11.4 ml) in dioxane (300 ml) is refluxed for 2 hours. The reaction mixture is poured into ice water and extracted with ether. The ether extracts are washed with water, dried (MgSO$_4$), and evaporated to give the title compound (5.2 g, mp 183°-185°). The analytical sample is prepared by recrystallization from 95% ethanol, mp 190°-191°, λ$^{KBr}$ 880 cm$^{-1}$.

Anal. Calc'd. C, 81.34; H, 5.12; Found C, 81.10; H, 5.40.

EXAMPLES 27 to 29

By refluxing a solution of a 7-substituted α-alkyl-α-hydroxyfluorene-2-acetic acid and sulfuric acid in dioxane in accordance with the procedure of Example 26, the corresponding α-alkylenefluorene-2-acetic acid as shown in Table IV below is formed.

hr. The reaction mixture is concentrated, acidified and extracted with ether. The ether extracts are washed with water, dried (MgSO$_4$) and evaporated to give the title compound.

Example 31

α-Hydroxy-α-methyl-fluorene-2-acetonitrile

A mixture of 2-acetylfluorene (5.32g.) in ether (20ml.) and water (40ml.) is cooled to 5° and agitated vigorously. Sodium cyanide (2.45g.) is added portionwise and the solution is then treated with conc. HCl (4.8ml.) while maintaining the temperature between 5°-10°. The mixture is then stirred for 2 hr. at room temperature, diluted with water and extracted with ether. The ether extracts are dried (MgSO$_4$) and evaporated to give the titled compound.

Examples 32 to 36

By reacting a 2-acyl fluorene as shown in the left hand column of Table V with sodium cyanide and hydrochloric acid in accordance with the procedure of Example 31, the α-hydroxy-fluorene-2-acetonitrile shown in the right hand column of Table V is obtained.

Table V

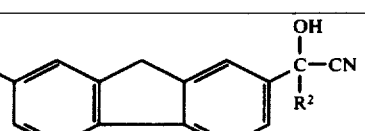

| Example | X | R² | X | R² |
|---|---|---|---|---|
| 32 | i-C₃H₇ | (S ring) | i-C₃H₇ | (S ring) |
| 33 | OC₂H₅ | (triangle) | OC₂H₅ | (triangle) |
| 34 | Br | (S pentagon) | Br | (S pentagon) |
| 35 | NH₂ | t-C₄H₉ | NH₂ | t-C₄H₉ |
| 36 | NO₂ | C₆H₁₃ | NO₂ | C₆H₁₃ |

Example 37

α-Methylene fluorene-2-acetic acid

The α-hydroxy-α-methyl-fluorene-2-acetonitrile is treated with conc. HCl (50ml.) and this solution is saturated with HCl and allowed to stand overnight. The solution is made alkaline with 50% aqueous sodium hydroxide, and then refluxed until the evolution of ammonia ceases. The solution is acidified and extracted with ether. The ether extracts are washed with water, dried (MgSO₄) and evaporated. The residue is dissolved in dioxane (150ml.) and sulfuric acid (5ml.) and refluxed for 2 hr. The reaction mixture is poured into ice water and extracted with ether. After drying and evaporation the title compound is obtained.

Examples 38 to 41

By reacting the 2-fluorene-hydroxyacetonitriles produced hereinbefore (and shown in Table VI) by the procedure of Example 37, the corresponding α-alkylene fluorene-2-acetic acid is obtained as shown in Table VI below.

Table VI

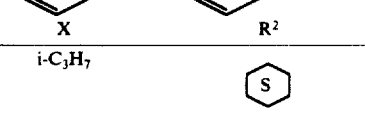

| Example | X | R² | X | R⁴ |
|---|---|---|---|---|
| 38 | t-C₄H₉ | C₇H₁₅ | t-C₄H₉ | C₆H₁₃ |
| 39 | OCH₃ | C₉H₁₉ | OCH₃ | C₈H₁₇ |
| 40 | Cl | C₁₁H₂₃ | Cl | C₁₀H₂₁ |
| 41 | NO₂ | CH₃ | NO₂ | H |

Example 42

α-Methyl fluorene-2-acetic acid

A solution of α-methylenefluorene-2-acetic acid (2.6g.) in dioxane (50ml.) is hydrogenated in the presence of 5% palladium on charcoal (800mg.). The mixture is filtered and the filtrate evaporated to dryness. The residue is sublimed to afford the title compound (2.6g.). The analytical sample is prepared by recrystallization from aqueous methanol, mp 181°-182°.

Anal. Calc'd. C,80,64; H,5.92; Found C,80.46; H,5.78.

Examples 43 to 45

By hydrogenating the α-alkylene fluorene-2-acetic acids prepared hereinbefore according to the procedure of Example 42, the corresponding acid is formed as shown in Table VII below.

Table VII

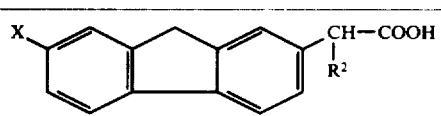

| Example | X | R² |
|---|---|---|
| 43 | Cl | CH₃ |
| 44 | NH₂ | C₂H₅ |
| 45 | NO₂ | C₃H₇ |

Example 46

α-Methylfluorene-2-acetonitrile

A solution of fluorene-2-acetonitrile (2g.) in dimethylformamide is treated with sodium hydride (415mg.) portionwise while stirring under nitrogen. After the evolution of hydrogen has ceased, the mixture is cooled to 10°-15° and treated dropwise with methyl iodide (2.82g.) in dimethylformamide (10ml.). After stirring for 30 minutes, the ice bath is removed and the mixture stirred at room temperature overnight. The reaction mixture is then poured into ice water and extracted with ether. The ether extracts are washed with water, dried (MgSO₄) and evaporated to give the title compound.

Examples 47 to 52

By reacting a fluorene-2-acetonitrile as shown in the left hand column of Table VIII below with sodium hydride and an alkyl halide as shown in the middle column, in accordance with the procedure described in Example 46, the product shown in the right hand column of Table VIII is obtained.

with water, dried (MgSO$_4$) and evaporated to give the title compound.

Example 57

Table VIII

| Example | X | R² | Hal | X | R² |
|---|---|---|---|---|---|
| 47 | C$_2$H$_5$ | CH$_3$ | Cl | C$_2$H$_5$ | CH$_3$ |
| 48 | OCH$_3$ | C$_2$H$_5$ | Br | OCH$_3$ | C$_2$H$_5$ |
| 49 | NH$_2$ | (thiophene) | I | NH$_2$ | (thiophene) |
| 50 | NO$_2$ | △ | Br | NO$_2$ | △ |
| 51 | Br | t-C$_4$H$_9$ | Cl | Br | t-C$_4$H$_9$ |
| 52 | NCH$_3$ H | C$_7$H$_{15}$ | Br | NCH$_3$ H | C$_7$H$_{15}$ |

Example 53

α-Methylfluorene-2-acetic acid 2.1g. of α-methylfluorene-2-acetonitrile is refluxed in 60% aqueous ethanol (50ml.) containing potassium hydroxide (5g.) until the evolution of ammonia ceases. The ethanol is evaporated and the aqueous solution acidified to pH 2.0 with HCl and extracted with ether. The ether extracts are washed with water, dried (MgSO$_4$) and evaporated to give the title compound.

Example 54

α-Methylfluorene-2-acetic acid

Following the procedure of Examples 46 and 53 but substituting methyl α-methylfluorene-2-acetic acid for α-methylfluorene-2-acetonitrile, there is obtained the title compound.

Example 55

α-Dimethylfluorene-2-acetic acid

Following the procedures of Examples 46 and 53 but substituting either methyl α-methylfluorene-2-acetic acid or α-methylfluorene-2-acetonitrile for the fluorene-2-acetonitrile there is obtained the title compound.

Example 56

α-Methylfluorene-2-acetic acid

A mixture of fluorene-2-carboxylic acid (3g.) in thionyl chloride (10ml.) is refluxed for 3 hr. and then evaporated. The acid chloride in ether (25ml.) is then added dropwise over a 15 minute period to a solution of diazoethane (3.42g.) in ether (175ml.) at −20°. The stirring is continued for an additional 15 minutes and the excess diazoethane removed in vacuo at −20°. The remaining solvent is removed at 0° to give the crude diazoketone. The diazoketone in benzyl alcohol (15ml.) and collidine (5ml.) is heated rapidly to 180°. After the evolution of nitrogen is complete, the cooled solution is extracted with ether. The ether extracts are washed with 10% HCl, water, dried (MgSO$_4$) and evaporated. The ester is 50% methanol (30ml.) containing potassium hydroxide (4g.) is refluxed for 3 hr., concentrated, and extracted with ether. The aqueous phase is acidified and extracted with ether. The ether extracts are washed 7-Hydroxyfluorene-2-acetic acid A solution of 14.5g. of methyl 7-aminofluorene-2-acetic acid in 380ml. of water containing 14ml. of concentrated hydrochloric acid is cooled to 2° and a solution of 3.63g. of sodium nitrite in 15ml. of water added dropwise while stirring. The diazonium solution is added over a 1 hour period while stirring to a refluxing solution of 1.1 liters of water containing 18ml. of sulfuric acid. The mixture is cooled and the solid collected by filtration. The solid is refluxed with 120ml. of 10% aqueous potassium hydroxide solution for 2 hr., and treated with Darco. The suspension is filtered, acidified with hydrochloric acid and the solid collected by filtration, dried, and crystallized from acetonitrile to give 9.4g. of the title compound, 240°–241° C.

Example 58

7-Hydroxyfluorene-2-acetic acid

A. Fermentation

Surface growth from a two week old agar slant of *Aspergillus niger* (ATCC-9142), the slant containing as nutrient medium (A):

|  | Grams |
|---|---|
| Glucose | 10 |
| Yeast Extract | 2.5 |
| K$_2$HPO$_4$ | 1 |
| Agar | 20 |
| Distilled Water to One Liter | |

Distilled Water to One Liter is suspended in 5ml. of 0.01% aqueous sodium lauryl sulfate solution. One ml. portions of this suspension are used to inoculate three 250ml. Erlenmeyer flaskes, each containing 50ml. of the following sterilized Medium (B):

|  | Grams |
|---|---|
| Glucose | 30 |
| Soy Bean Meal | 20 |
| Soy Bean Oil | 2.0 |
| CaCO$_3$ | 2.5 |
| Distilled Water to One Liter | |

After approximately 96 hours incubation at 25° C with continuous rotary agitation (280 cycles/minute; 2° inch stroke), 5% (vol/vol) transfers are made to twenty 250ml. Erlenmeyer flasks each containing 50ml. of the following sterilized medium (C);

|  | Grams |
| --- | --- |
| Corn Steep Liquor | 6 |
| NH$_4$H$_2$PO$_4$ | 3 |
| Yeast Extract | 2.5 |
| Dextrose | 10 |
| CaCO$_3$ | 2.5 |
| Distilled Water to One Liter | |

After 24 hours of incubation, using the same conditions as described above, substrate (200 micrograms/ml.) is then added by supplementing each flask with 0.25ml. of a sterile solution (40mg./ml.) of fluorene-2-acetic acid in N,N-dimethylformamide. A total of 200 mg. of fluorene-2-acetic acid is fermented.

After approximately 6 days of further incubation using identical conditions as described above the contents of the flasks are pooled and the broth is adjusted to pH 2.5 with 12N H$_2$SO$_4$. The acidified broth is then filtered through a Seitz clarifying pad. The flasks, mycelium and pad are washed with successive 100ml. portions of warm water. The combined filtrate and washings have a volume of 1500ml.

B. Isolation

The thus obtained filtrate is extracted with ethyl acetate. The extracts are washed with 8% salt solution, dried and evaporated. The residue is crystallized from ethyl acetate to give 42mg. of the title compound, mp 235.5°–237.5°d. The analytical sample is prepared by recrystallization from ethyl acetate, mp 236°–238°d; λ $^{KBr}$ 5.84μ; τ $_{DMSO}$$^{TMS}$ τ 6.44 (S,2.CH$_2$-CO$_2$H) and 6.23 αS,9-CH$_2$).

Anal. Calcd. for C$_{15}$H$_{12}$O$_3$: C,74.99; H,5.03; Found: C,74.72; H,4.80. acetone-isopropyl ether, mp 136–137°;λ $^{KBr}$ 5.85μ; τ$_{DMSO}$$^{TMS}$

EXAMPLE 59

Methyl 7-Hydroxyfluorene-2-acetic acid

A solution of 83mg. of 7-hydroxyfluorene-2-acetic acid in 2ml. of methanol and 5ml. of ether is treated with an excess of diazomethane in ether. After 20 min. at room temperature, the mixture is treated with several drops of acetic acid and evaporated. The residue is plate chromatographed on silica gel using chloroform as the developing solvent. The major band (UV) is eluted with ethyl acetate, evaporated, and the residue crystallized from acetone-isopropyl ether to give 36mg. of the title compound, mp 135.5°–136.5°. The analytical sample is prepared by recrystallization from acetone-isopropyl ether, mp 136–137°; λ $^{KBr}$ 5.85μ; τ$_{CDCl_3}$ $^{TMS}$ 6.31 (S, 2-CH$_2$CO$_2$CH$_3$).

Anal Calc'd. for C$_{16}$H$_{14}$O$_3$: C,75.57; H,5.55; Found: C,75.72; H,5.75.

EXAMPLE 60

Methyl 7-Methoxyfluorene-2-acetic acid A mixture of 59 mg. of methyl 7-hydroxyfluorene-2-acetic acid, 1.3 g. of potassium carbonate, and 0.5 ml. methyl iodide in 11 ml. of acetone is refluxed for 22 hr., filtered and the solid washed with additional acetone. The filtrate is evaporated and the residue plate chromatographed on silica gel employing chloroform-hexane (2:1) as the developing solvent. Elution of the least polar band with ethyl acetate, evaporation and crystallization of the residue from ethyl acetate-isopropyl ether gives 17 mg. of the title compound, mp 114°–115°. Recrystallization from ethyl acetate-isopropyl ether gives the analytical sample, mp 114.5°–11.5°; λ $^{KBr}$5.80μ.

Anal Calc'd. for C$_{17}$H$_{16}$O$_3$: C,76.10; H,6.01; Found: C,75.90; H,6.13.

EXAMPLE 61

7-Methoxyfluorene-2-acetic acid

A solution of 20mg. of methyl 7-methoxyfluorene-2-acetic acid in 7ml. of ethanol containing 0.5ml. of 50% aqueous potassium hydroxide solution is refluxed overnight. The mixture is acidified and the solid collected by filtration. Crystallization from chloroform-isopropyl ether gives 8mg. of the title compound, mp 200°–202°. The analytical sample is prepared by tube to tube evaporative distillation, mp 203–205°; λ $^{KBr}$ 5.93μ.

Anal Calc'd. for C$_{16}$H$_{14}$O$_3$: C,75.57; H,5.55; Found: C,75.79; H,5.75.

EXAMPLE 62

2-(7-Methoxy-2-fluorenyl)propionic acid

Following the procedures outlined in the four previous examples, but substituting α-methylfluorene-2-acetic acid for fluorene-2-acetic acid there is obtained the title compound.

EXAMPLE 63

7-Nitro-α-methylfluorene-2-acetic acid

A suspension of α-methylfluorene-2-acetic acid (11.9 g) in acetic acid (10 ml) is stirred and heated to 60°, and then treated dropwise with concentrated nitric acid (12.7 ml) over a 0.5 hour period. The temperature is kept at 80° by cooling. After the addition is completed, the mixture is heated at 80° for 15 minutes then cooled. The crystalline material is collected by filtration to give 7.5 g, mp 206°–209° of the titled product. The analytical sample is prepared by recrystallization from acetic acid, mp 215°–216°.

Anal. Calc'd. for C$_{16}$H$_{13}$NO$_4$: C, 67.84; H, 4.63; N, 4.95; Found: C, 68.07; H, 4.86; N, 4.82.

EXAMPLE 64

7-Nitro-α-methylfluorene-2-acetic acid methyl ester

A mixture of 7-nitro-α-methylfluorene-2-acetic acid (16.8 g) in thionyl chloride (160 ml) is refluxed for 1 hour and excess thionyl chloride removed by distillation. The residue is treated with methanol (400 ml) and refluxed for 2.5 hours and then cooled. The solid is collected by filtration to give 13.2 g, mp 105°–107° of the titled product. The analytical sample is prepared by recrystallization from methanol, mp 108°–110°. p Anal. Calc'd. for C$_{17}$H$_{15}$NO$_4$: C, 68.67; H, 5.08; N, 4.71; Found: C, 68.59; H, 5.05; N, 4.97.

EXAMPLE 65

7-Hydroxy-α-methylfluorene-2-acetic acid

A slurry of 7-nitro-α-methylfluorene-2-acetic acid methyl ester (13.1 g) in 78% ethanol (400 ml) is treated with a solution of calcium chloride (4.5 g) in water (6.1 ml), zinc dust (127 g) and charcoal (4.6 g) and the mixture refluxed for 2.5 hours. The hot mixture is filtered and the cake washed with hot 78% ethanol. The filtrate is diluted with water (800 ml) and extracted with chloroform. The chloroform extracts are dried ($MgSO_4$) and evaporated to give 10.1 g of 7-amino-α-methylfluorene-2-acetic acid methyl ester.

The ester is dissolved in water (300 ml) containing concentrated HCl (11ml) with the aid of heat. The solution is cooled to 3°, stirred and treated dropwise with a solution of sodium nitrite (2.84 g) in water (15 ml) over a 30 minute period. The resulting diazonium solution is then added dropwise over a 1 hour period to boiling water (800 ml) containing concentrated sulfuric acid (13 ml), and then stirred for 30 minutes and cooled. The precipitate is collected by filtration and heated in 10% aqueous potassium hydroxide containing charcoal for 1 hour, cooled and acidified with 4N HCl. The solid is collected by filtration to give 8.0 g, mp 205°–207° of the tilted product. The analytical sample is prepared by sublimation, mp 218°–219°.

Anal. Calc'd for $C_{16}H_{14}O_3$: C, 75.57; H, 5.55; Found: C, 75.25; H, 5.75.

EXAMPLE 66

7-Methoxy-α-methylfluorene-2-acetic acid methyl ester

A solution of 7-hydroxy-α-methylfluorene-2-acetic acid (10.8 g) in methanol is treated with an excess of ethereal diazomethane to prepare the methyl ester. The ester is dissolved in acetone (550 ml) containing potassium carbonate (110 g) treated with methyl iodide (83 ml) and refluxed overnight. The mixture is filtered and the filtrate evaporated to dryness. The residue is treated with ethyl acetate and filtered to give the crude product. A portion of this material is plate chromatographed on silica gel employing chloroform-hexane (1:1) as the developing solvent. Elution of the least polar band with ethyl acetate, evaporation and crystallization of the residue from acetone-isopropyl ether gave the title product (mp 98.5°–100.5°). The analytical sample is prepared by recrystallization from acetone-isopropyl ether, mp 101°–103°.

Anal. Calc'd for $C_{18}H_{18}O_3$: C, 76.57; H, 6.43; Found: C, 76.55; H, 6.30.

EXAMPLE 67

7-Methoxy-α-Methylfluroene-2-Acetic Acid

The bulk of the crude product from the above reaction (Example 66) is refluxed in ethanol (200 ml) containing 40% aqueous potassium hydroxide solution (40 ml) for 2 hours. The ethanol is removed by evaporation and the insoluble potassium salt suspended in water (100 ml) and acidified with 6N HCl. The aqueous is extracted with ethyl acetate, and the extracts dried ($MgSO_4$) and evaporated to give 9.5 g, mp. 179°–181° of the titled product. The analytical sample is prepared by recrystallization from ethyl acetate, mp 183°–184°.

Anal. Calc'd for $C_{17}H_{16}O_3$: C, 76.10; H, 6.08; Found: C, 75.88; H, 6.11.

EXAMPLE 68

7-Hydroxy-α-methylfluorene-2-acetic acid

A. Fermentation

Surface growth from a two week old agar slant of *Aspergillus niger* (ATCC-9142), the slant containing as nutrient medium (A):

|  | Grams |
| --- | --- |
| Glucose | 10 |
| Yeast extract | 2.5 |
| $K_2HPO_4$ | 1 |
| Agar | 20 |
| Distilled Water to One liter | | is suspended in 5 ml of 0.01% aqueous sodium lauryl sulfate solution. One ml portions of this suspension are used to inoculate three 250 ml Erlenmeyer flasks each containing 50 ml of the following sterilized medium (B):

|  | Grams |
| --- | --- |
| Glucose | 30 |
| Soy Bean Meal | 20 |
| Soy Bean Oil | 2.0 |
| $CaCO_3$ | 2.5 |
| Distilled Water to One Liter | |

After approximately 96 hours incubation at 25° C with continuous rotary agitation (280 cycles/minute; 2 inch stroke), 5% (vol/vol) transfers are made to twenty 250 ml Erlenmeyer flasks each containing 50 ml of the following sterilized medium (C):

|  | Grams |
| --- | --- |
| Corn Steep Liquor | 6 |
| $NH_4H_2PO_4$ | 3 |
| Yeast Extract | 2.5 |
| Dextrose | 10 |
| $CaCO_3$ | 2.5 |
| Distilled Water to One Liter | |

After 24 hours of incubation, using the same conditions as described above, substrate is then added by supplementing each flask with 0.25 ml of a sterile solution (60 mg/ml) of α-methylfluorene-2-acetic acid in N,N-dimethylformamide. A total of 300 mg of α-methylfluorene-2-acetic acid is fermented.

After approximately six days of further incubation using identical conditions as described above the contents of the flasks are pooled and the broth is adjusted to pH 2.5 with 12N $H_2SO_4$. The acidified broth is then filtered through a Seitz clarifying pad. The flasks, mycelium and pad are washed with successive 100 ml portions of warm water. The combined filtrate and washings have a volume of 1500 ml.

B. Isolation

The thus obtained filtrate is extracted with ethyl acetate. The extracts are washed with 8% salt solution, dried and evaporated. The residue is crystallized from ethyl acetate to give 98 mg of the title compound, mp 218°–220°.

The following example demonstrates the resolution of α-methylfluorene-2-acetic acid into its optical isomers:

EXAMPLE 69

A solution of 34.0 g of dl-α-methylfluorene-2-acetic acid in 300 ml of ethyl acetate, is treated with 17.8 g of d-α-methylbenzylamine. The suspension is diluted with additional ethyl acetate (200 ml), refluxed and treated with methanol (about 400 ml) until solution is achieved. The solution is concentrated to about ⅓ its original volume, allowed to stand at room temperature overnight, and the resulting solid collected by filtration. The salt is recrystallized from ethyl acetate-methanol several times, and then converted to the free acid in the following manner. The salt is partitioned between ethyl acetate and 10% hydrochloric acid and the ethyl acetate layer separated and the aqueous washed with more ethyl acetate. The combined organic layers are dried (Na$_2$SO$_4$) and evaporated to give 5.0 of the d isomer, mp 178°-179°, $[\alpha]_D^{25} = +56\pm1°$.

The mother liquor from the first crystallization is evaporated a dryness and converted to the free acid ($[\alpha]_D^{25} = -22°$). This acid is treated with 1-α-methylbenzylamine and the resulting salt recrystallized several times, and then converted in the same manner as described above into the free acid to give 5.0 g of the l-isomer, mp 179°-181°, $[\alpha]_D^{25} = -56\pm1°$.

The following examples show the anti-inflammatory activity of fluorene-2-acetic acid and 7-chloro-fluorene-2-acetic acid as determined by carrageenin-induced edema assay.

EXAMPLES 70 and 71

The procedure for these experiments is to first orally administer the test compound to a rat. Two hours later a solution of carrageenin is injected into the plantar surface of the hind paw of the rat. Three hours after the injection (5 hours after administration of the drug) the edema in the treated paw is measured by weighing the paws. To establish the baseline, the weight of the contralateral paw is determined. A dose-response curve is established, and the activity of the drug is recorded as the calculated dose that produces 50 percent inhibition (ID$_{50}$) of the edema.

| Example | | ID$_{50}$(mg/kg) |
|---|---|---|
| 70 | fluorene-2-acetic acid | 67 |
| 71 | 7-chloro-fluorene-2-acetic acid- | approximately 150 |

What is claimed is:

1. A compound having the structure

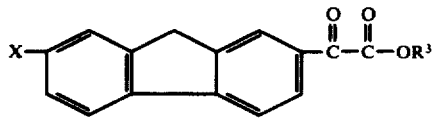

wherein X is selected from the group consisting of hydrogen, hydroxyl, lower alkyl, lower alkoxy, halogen, amino, trifluoromethyl and nitro; and R$^3$ is selected from the group consisting of hydrogen and lower alkyl.

2. A compound in accordance with claim 1 wherein R$^3$ is hydrogen.

3. A compound in accordance with claim 1 wherein R$^3$ is lower alkyl.

4. A compound in accordance with claim 1 wherein X is hydrogen or lower alkyl.

5. The compound in accordance with claim 1 having the name ethyl fluorene-2-glyoxylic acid.

* * * * *